United States Patent
Jameson et al.

(10) Patent No.: US 7,413,435 B2
(45) Date of Patent: Aug. 19, 2008

(54) FUEL DELIVERY METHOD FOR MELTING PLATE CANDLE

(75) Inventors: Elizabeth J. Jameson, Racine, WI (US); Chris A. Kubicek, East Troy, WI (US); Thomas J. Szymczak, Franksville, WI (US); Padma Prabodh Varanasi, Racine, WI (US); Joel E. Adair, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 409 days.

(21) Appl. No.: 10/938,453

(22) Filed: Sep. 10, 2004

(65) Prior Publication Data

US 2006/0057524 A1    Mar. 16, 2006

(51) Int. Cl.
*F23D 3/16* (2006.01)
(52) U.S. Cl. .................................. 431/292; 431/291
(58) Field of Classification Search .................. 431/292, 431/291, 289, 288, 126, 35, 33; *F23D 3/16*
See application file for complete search history.

(56) References Cited

U.S. PATENT DOCUMENTS

| 213,184 | A | 3/1879 | Frick |
| 405,786 | A | 6/1889 | Ludde |
| 407,051 | A | 7/1889 | Baumer |
| 408,973 | A | 8/1889 | Heller |

(Continued)

FOREIGN PATENT DOCUMENTS

CA    2208145    12/1998

(Continued)

OTHER PUBLICATIONS

International Candle House catalog (1966-67); Bobeshes pp. 54-55.

(Continued)

*Primary Examiner*—Steve McAllister
*Assistant Examiner*—Chuka C Ndubizu
(74) *Attorney, Agent, or Firm*—McCracken & Frank LLP (57) ABSTRACT

The present invention relates to melting plate candles which employ heat conductive elements to distribute heat from a burning flame at a wick to a support plate for a solid fuel and to the body of said solid fuel, so as to more rapidly liquefy the solid fuel, such as paraffin wax, and to more uniformly and intensely heat such fuels to increase the efficiency of consumption thereof and to more rapidly release volatile materials contained within said fuels. The heat conductive support plate is configured so as to have a capillary pedestal upon the surface thereof, which cooperatively engages a wick holder comprising a preferably consumable wick and heat conductive fins which conduct heat from a flame upon said wick to said support plate. The wick holder also provides capillary fins by which liquified fuel is transported from said support plate to said flame, Said wick holder further engages said capillary pedestal in such a locking manner as to resist accidental removal from said pedestal. The fuel may be provided in various forms, configured to cooperatively engage said wick holder and support plate, and may comprise various volatile materials. The capillary pedestal, in conjunction with the wick holder, causes rapid and complete flow of the liquefied fuel to said wick.

21 Claims, 4 Drawing Sheets

U.S. PATENT DOCUMENTS

| | | | |
|---|---|---|---|
| 484,210 A | 10/1892 | Ludde | |
| 779,644 A | 1/1905 | Ferrier | |
| 837,240 A | 11/1906 | Mulkerins | |
| 1,044,256 A | 11/1912 | Satter | |
| D43,845 S | 4/1913 | Hirschfeld | |
| 1,195,657 A | 8/1916 | Chersky | |
| D49,902 S | 11/1916 | Labaree et al. | |
| 1,229,140 A | 6/1917 | Ritter | |
| 1,316,624 A | 9/1919 | Lucas | |
| 1,320,109 A | 10/1919 | Wooster | |
| 1,336,635 A | 4/1920 | Knapp | |
| 1,390,389 A | 9/1921 | Rosenfeld | |
| 1,484,964 A | 2/1924 | Benneville | |
| D67,108 S | 4/1925 | Steeple | |
| 1,640,734 A | 8/1927 | Smith | |
| D75,463 S | 6/1928 | Bach | |
| D80,971 S | 4/1930 | Sakier | |
| D83,100 S | 1/1931 | Gisolfi | |
| D110,902 S | 8/1938 | Loesch | |
| D119,587 S | 3/1940 | Fuerst | |
| 2,234,903 A | 3/1941 | Muench | |
| 2,237,523 A | 4/1941 | Damon | |
| 2,246,346 A | 6/1941 | Wells | |
| 2,254,906 A | 9/1941 | Petrulis | |
| 2,324,753 A | 7/1943 | Alexiade | |
| 2,354,343 A | 7/1944 | Webber et al. | |
| 2,393,767 A | 1/1946 | Gould | |
| 2,462,440 A | 2/1949 | Tierney | |
| 2,494,995 A | 1/1950 | Gardner | |
| 2,713,256 A | 7/1955 | Oesterle | |
| 2,758,460 A | 8/1956 | Ciano | |
| 2,775,006 A | 12/1956 | Kranc | |
| 2,809,512 A | 10/1957 | Hartnett | |
| RE24,423 E | 2/1958 | Oesterle et al. | |
| 3,121,316 A | 2/1964 | Wilson | |
| D206,946 S | 2/1967 | Knodt | |
| D208,064 S | 7/1967 | Quistgaard et al. | |
| D208,097 S | 7/1967 | Henn | |
| 3,565,281 A | 2/1971 | Collie | |
| 3,689,616 A * | 9/1972 | Kelley | 264/68 |
| D226,240 S | 1/1973 | Twedt | |
| 3,730,674 A * | 5/1973 | Gross | 431/288 |
| 3,741,711 A | 6/1973 | Bryant | |
| 3,749,904 A | 7/1973 | Graff | |
| 3,762,857 A | 10/1973 | Andeweg | |
| D229,852 S | 1/1974 | Lindblad | |
| 3,873,263 A | 3/1975 | DeCroix | |
| D236,064 S | 7/1975 | Balbo | |
| 3,898,039 A | 8/1975 | Lin | |
| 3,910,753 A * | 10/1975 | Lee | 431/290 |
| 3,932,113 A | 1/1976 | Thrush | |
| 3,994,502 A | 11/1976 | Lombardi | |
| 4,013,397 A | 3/1977 | Neugart | |
| 4,019,856 A | 4/1977 | Lacroix | |
| D247,635 S | 3/1978 | Maxwell | |
| D248,499 S | 7/1978 | Ulrich et al. | |
| D248,500 S | 7/1978 | Ulrich et al. | |
| 4,102,634 A | 7/1978 | Crisp | |
| D248,787 S | 8/1978 | Ulrich et al. | |
| D248,788 S | 8/1978 | Ulrich et al. | |
| D248,789 S | 8/1978 | Ulrich et al. | |
| D253,432 S | 11/1979 | Van Koert | |
| D253,732 S | 12/1979 | Van Koert | |
| 4,185,953 A | 1/1980 | Schirneker | |
| 4,206,500 A | 6/1980 | Neil | |
| 4,206,560 A | 6/1980 | Sefried, II | |
| 4,224,017 A | 9/1980 | Kayne | |
| D264,385 S | 5/1982 | Meyer | |
| 4,332,548 A | 6/1982 | Linton et al. | |
| 4,381,914 A | 5/1983 | Ferguson | |
| 4,427,366 A | 1/1984 | Moore | |
| 4,477,249 A | 10/1984 | Ruzek et al. | |
| 4,524,408 A | 6/1985 | Minera | |
| 4,551,794 A | 11/1985 | Sandell | |
| 4,557,687 A | 12/1985 | Schirneker | |
| 4,568,269 A | 2/1986 | Lin | |
| 4,568,270 A | 2/1986 | Marcus et al. | |
| 4,588,618 A | 5/1986 | Wolfe | |
| D292,525 S | 10/1987 | Van Deelen | |
| 4,755,135 A * | 7/1988 | Kwok | 431/290 |
| 4,781,895 A | 11/1988 | Spector | |
| 4,804,323 A | 2/1989 | Kim | |
| 4,917,597 A * | 4/1990 | Henze | 431/289 |
| D312,507 S | 11/1990 | Thoreson | |
| 4,983,119 A | 1/1991 | Lin | |
| 5,015,175 A | 5/1991 | Lee | |
| D320,266 S | 9/1991 | Kunze | |
| 5,069,617 A | 12/1991 | Lin | |
| 5,078,591 A | 1/1992 | Depres | |
| 5,078,945 A | 1/1992 | Byron | |
| 5,086,380 A | 2/1992 | Hedner, Jr. | |
| D325,077 S | 3/1992 | Kearnes | |
| 5,101,328 A | 3/1992 | Hai | |
| 5,174,645 A | 12/1992 | Chung | |
| 5,193,994 A | 3/1993 | Schirneker | |
| 5,338,187 A | 8/1994 | Elharar | |
| 5,363,590 A | 11/1994 | Lee | |
| D355,266 S | 2/1995 | Caplette et al. | |
| D356,472 S | 3/1995 | Jaworski | |
| 5,425,633 A | 6/1995 | Cole | |
| D360,461 S | 7/1995 | Gillespie | |
| D369,871 S | 5/1996 | Lui | |
| D371,212 S | 6/1996 | Hardy et al. | |
| D376,002 S | 11/1996 | Upson | |
| D377,402 S | 1/1997 | Perkins | |
| D383,944 S | 9/1997 | Lillelund et al. | |
| 5,690,484 A | 11/1997 | Leonard et al. | |
| D390,676 S | 2/1998 | Hollington | |
| D391,119 S | 2/1998 | Rapaz | |
| D393,910 S | 4/1998 | Chambers et al. | |
| D394,513 S | 5/1998 | Davis | |
| 5,807,096 A | 9/1998 | Shin et al. | |
| D399,298 S | 10/1998 | Whitehead | |
| 5,840,246 A | 11/1998 | Hammons et al. | |
| 5,842,850 A * | 12/1998 | Pappas | 431/291 |
| 5,843,194 A | 12/1998 | Spaulding | |
| 5,871,553 A | 2/1999 | Spaulding | |
| D410,756 S | 6/1999 | Kleinberg | |
| 5,921,767 A | 7/1999 | Song | |
| 5,927,959 A | 7/1999 | Johnson | |
| 5,939,005 A | 8/1999 | Materna | |
| 5,951,278 A | 9/1999 | Young et al. | |
| 5,955,034 A | 9/1999 | Zaunbrecher et al. | |
| 5,955,958 A | 9/1999 | Lu | |
| 5,961,967 A | 10/1999 | Powell et al. | |
| D416,099 S | 11/1999 | Hardy | |
| D416,341 S | 11/1999 | Allen | |
| 5,980,241 A | 11/1999 | Schirneker | |
| 6,019,804 A | 2/2000 | Requejo et al. | |
| 6,033,209 A | 3/2000 | Shin et al. | |
| D422,180 S | 4/2000 | Sundberg | |
| 6,050,812 A | 4/2000 | Chuang | |
| D425,220 S | 5/2000 | Klett et al. | |
| D425,636 S | 5/2000 | Freeman | |
| 6,059,564 A | 5/2000 | Morris | |
| 6,062,847 A | 5/2000 | Pappas | |
| 6,068,472 A | 5/2000 | Freeman et al. | |
| D426,902 S | 6/2000 | Hardy et al. | |
| 6,074,199 A | 6/2000 | Song | |
| 6,079,975 A | 6/2000 | Conover | |
| 6,099,877 A | 8/2000 | Schuppan | |
| D430,943 S | 9/2000 | Zutler | |
| D433,168 S | 10/2000 | Cousins | |
| 6,129,771 A | 10/2000 | Ficke et al. | |

| | | |
|---|---|---|
| 6,152,728 A | 11/2000 | Griffel |
| D435,100 S | 12/2000 | Pesu et al. |
| D436,415 S | 1/2001 | Hardy |
| 6,214,063 B1 | 4/2001 | DeStefano et al. |
| D443,080 S | 5/2001 | Klett et al. |
| D443,081 S | 5/2001 | Klett et al. |
| D443,082 S | 5/2001 | Klett et al. |
| D443,101 S | 5/2001 | Williamson |
| 6,231,336 B1 | 5/2001 | Chen |
| 6,241,362 B1 | 6/2001 | Morrison |
| 6,241,513 B1 | 6/2001 | Jeneral |
| D445,030 S | 7/2001 | Croft et al. |
| D445,337 S | 7/2001 | Croft et al. |
| 6,267,584 B1 | 7/2001 | Zou |
| 6,270,339 B1 | 8/2001 | Zou |
| 6,273,710 B1 | 8/2001 | Zou |
| 6,276,925 B1 | 8/2001 | Varga |
| D447,418 S | 9/2001 | Bezek et al. |
| 6,290,489 B1 | 9/2001 | Seidler |
| D448,867 S | 10/2001 | Manocheo et al. |
| 6,296,477 B1 | 10/2001 | Lin |
| 6,299,435 B1 | 10/2001 | Freeman et al. |
| D450,395 S | 11/2001 | Bellenger |
| D450,865 S | 11/2001 | Bellenger et al. |
| 6,328,935 B1 | 12/2001 | Buccellato |
| 6,361,311 B1 | 3/2002 | Smith |
| D455,486 S | 4/2002 | Makino |
| D455,846 S | 4/2002 | Araujo |
| D456,539 S | 4/2002 | Leeds |
| 6,371,756 B1 | 4/2002 | Toohey |
| D459,498 S | 6/2002 | Araujo |
| 6,398,544 B2 | 6/2002 | Wright et al. |
| D461,916 S | 8/2002 | Araujo |
| D462,132 S | 8/2002 | Papai |
| 6,428,311 B1 | 8/2002 | Bernardo |
| 6,439,471 B2 | 8/2002 | Ehrlich et al. |
| D462,793 S | 9/2002 | Freeman et al. |
| 6,450,802 B1 | 9/2002 | Steck |
| 6,454,561 B1 | 9/2002 | Colthar et al. |
| D464,745 S | 10/2002 | Mangini et al. |
| 6,468,071 B2 | 10/2002 | Zou |
| D465,587 S | 11/2002 | Papai |
| D466,236 S | 11/2002 | Papai |
| 6,488,494 B2 | 12/2002 | Lee |
| 6,491,516 B1 | 12/2002 | Tal et al. |
| D469,550 S | 1/2003 | Moeller |
| D469,893 S | 2/2003 | Shen |
| 6,520,770 B2 | 2/2003 | Zou |
| D471,299 S | 3/2003 | Papai |
| 6,531,063 B1 | 3/2003 | Rose |
| 6,537,063 B1 | 3/2003 | Pecoskie |
| 6,543,268 B2 | 4/2003 | Wright et al. |
| 6,544,302 B2 | 4/2003 | Berger et al. |
| 6,551,365 B2 | 4/2003 | Berger et al. |
| 6,554,448 B2 | 4/2003 | Carpenter et al. |
| D474,854 S | 5/2003 | Lam |
| 6,568,934 B1 | 5/2003 | Butler |
| 6,575,613 B2 | 6/2003 | Brown et al. |
| 6,579,089 B1 | 6/2003 | Iu |
| 6,592,637 B2 | 7/2003 | McGee et al. |
| 6,595,771 B2 | 7/2003 | Chu |
| 6,616,308 B2 | 9/2003 | Jensen et al. |
| D481,143 S | 10/2003 | McMinn |
| D481,473 S | 10/2003 | Walsh |
| 6,630,110 B2 | 10/2003 | Urfig |
| 6,648,631 B2 * | 11/2003 | Wright et al. ............... 431/291 |
| D485,624 S | 1/2004 | Kitamura |
| 6,688,880 B1 | 2/2004 | Pangle |
| 6,695,611 B2 | 2/2004 | Lee |
| D487,687 S | 3/2004 | Shields, Jr. |
| 6,709,266 B2 | 3/2004 | Jensen |
| 6,730,137 B2 | 5/2004 | Pesu et al. |
| 6,733,279 B2 | 5/2004 | Thigpen et al. |
| D491,288 S | 6/2004 | Young |
| D493,548 S | 7/2004 | Goldman |
| D495,437 S | 8/2004 | Barbera |
| D495,438 S | 8/2004 | Barbera et al. |
| 6,769,905 B2 | 8/2004 | Gray et al. |
| 6,780,382 B2 | 8/2004 | Furner et al. |
| D497,680 S | 10/2004 | McMinn |
| 6,802,707 B2 | 10/2004 | Furner |
| 6,808,388 B2 | 10/2004 | Lee |
| 6,857,869 B1 | 2/2005 | Sun |
| 6,863,525 B2 | 3/2005 | Byrd |
| 6,923,639 B2 | 8/2005 | Pesu et al. |
| 2001/0031438 A1 | 10/2001 | Hannington et al. |
| 2002/0066789 A1 | 6/2002 | Yen |
| 2002/0068009 A1 | 6/2002 | Laudamiel-Pellet |
| 2002/0068010 A1 | 6/2002 | Laudamiel-Pellet |
| 2002/0093834 A1 | 7/2002 | Yu |
| 2002/0102187 A1 | 8/2002 | Bellenger et al. |
| 2002/0119413 A1 | 8/2002 | Cheng |
| 2002/0127507 A1 | 9/2002 | Long |
| 2003/0027091 A1 | 2/2003 | Brandt |
| 2003/0064336 A1 | 4/2003 | Welch |
| 2003/0134246 A1 | 7/2003 | Gray et al. |
| 2003/0162142 A1 | 8/2003 | Bennetts et al. |
| 2003/0175148 A1 | 9/2003 | Kvietok |
| 2004/0007787 A1 | 1/2004 | Kvietok |
| 2004/0009103 A1 | 1/2004 | Westring |
| 2004/0009447 A1 | 1/2004 | Decker |
| 2004/0016818 A1 | 1/2004 | Murdell |
| 2004/0028551 A1 | 2/2004 | Kvietok |
| 2004/0029061 A1 | 2/2004 | Dibnah et al. |
| 2004/0033171 A1 | 2/2004 | Kvietok |
| 2004/0033463 A1 | 2/2004 | Pesu et al. |
| 2004/0128879 A1 | 7/2004 | Lu |
| 2004/0160764 A1 | 8/2004 | Lee |
| 2004/0223871 A1 | 11/2004 | Woo |
| 2004/0223943 A1 | 11/2004 | Woo |
| 2004/0229180 A1 | 11/2004 | Furner |
| 2004/0241053 A1 | 12/2004 | Thompson |
| 2004/0265164 A1 | 12/2004 | Woo |
| 2005/0019238 A1 | 1/2005 | Hart et al. |
| 2005/0037306 A1 | 2/2005 | Nakatsu |
| 2005/0079463 A1 | 4/2005 | Yu |
| 2006/0057521 A1 | 3/2006 | Kubicek et al. |
| 2006/0057522 A1 | 3/2006 | Kubicek et al. |
| 2006/0057523 A1 | 3/2006 | Kubicek et al. |
| 2006/0057526 A1 | 3/2006 | Kubicek et al. |
| 2006/0057528 A1 | 3/2006 | Kubicek et al. |
| 2006/0057529 A1 | 3/2006 | Kubicek et al. |
| 2006/0084021 A1 | 4/2006 | Kubicek |

FOREIGN PATENT DOCUMENTS

| | | |
|---|---|---|
| DE | 2440068 | 3/1976 |
| DE | 3302591 | 8/1984 |
| DE | 3403604 | 8/1985 |
| DE | 4203644 | 8/1993 |
| DE | 4241292 | 5/1994 |
| DE | 4314122 | 11/1994 |
| DE | 195 48 958 | 5/1996 |
| DE | 195 08 962 | 9/1996 |
| DE | 102004011919 | 6/2005 |
| EP | 0146247 | 6/1985 |
| EP | 1054054 | 11/2000 |
| EP | 1 336 799 | 8/2003 |
| FR | 2628825 | 3/1988 |
| GB | 161342 | 4/1921 |
| GB | 1514338 | 6/1978 |
| GB | 2 239 942 | 7/1991 |
| JP | 362220594 | 9/1987 |
| JP | 406212189 | 8/1994 |
| JP | 408185710 | 7/1996 |
| JP | 2003-213292 | 7/2003 |

| | | |
|---|---|---|
| WO | WO 89/06141 | 7/1989 |
| WO | WO 95/12783 | 5/1995 |
| WO | WO 96/02794 | 2/1996 |
| WO | WO 99/17055 | 4/1999 |
| WO | WO 99/45322 | 9/1999 |
| WO | WO 00/32989 | 6/2000 |
| WO | WO 01/46618 | 6/2001 |
| WO | WO 2004/008026 | 1/2004 |
| WO | WO 2004/083349 | 9/2004 |
| WO | WO 2004/083718 | 9/2004 |
| WO | WO 2004/090417 | 10/2004 |

OTHER PUBLICATIONS

Pourette Catalog 1998; p. 12.
Prices London Candlemakers; http:www.prices-candles.co.uk/mainpage.htm; 1 page, printed Apr. 21, 2005.
Prices London Candlemakers; http:www.prices-candles.co.uk/catalogue/Accessories/Accessories%20Page%2008.jpg; 1 page; printed Apr. 21, 2005.
Two (2) photos of Price's "Coral Bay Fragranced Bathroom" product taken Jan. 1, 1999.
Stephanie Reiser Wrought Iron—"Welcome to CourtingCandle.com!" http://www/courtingcandle.com; 1 page printed on May 12, 2004.
Intl. Search Report dated Oct. 13, 2006, Appl. No. PCT/US 2006/020218 (4315PCT).
Intl. Search Report dated Jul. 27, 2006, Appl. No. PCT/US 2005/032266 (4033 PCT).
U.S. Appl. No. 09/742,631, Office Action dated Aug. 18, 2003.
U.S. Appl. No. 09/747,525, Office Action dated Sep. 9, 2003.
U.S. Appl. No. 09/747,525, Office Action dated May 20, 2003.
U.S. Appl. No. 09/747,525, Office Action dated Jan. 10, 2003.
U.S. Appl. No. 09/747,525, Office Action dated Jul. 2, 2002.
U.S. Appl. No. 09/747,525, Office Action dated Oct. 1, 2001.
U.S. Appl. No. 10/780,028, Office Action dated Oct. 4, 2006.
U.S. Appl. No. 10/780,028, Office Action dated Apr. 11, 2006.
U.S. Appl. No. 10/780,028, Office Action dated 10-18-06-2006.
U.S. Appl. No. 10/938,434, Office Action dated Jul. 17, 2006.
U.S. Appl. No. 10/978,744, Office Action dated Jul. 19, 2006.
U.S. Appl. No. 10/978,646, Office Action dated Aug. 3, 2006.
U.S. Appl. No. 10/978,744, Final Office Action dated Nov. 13, 2006.
U.S. Appl. No. 10/938,434, Final Office Action dated Nov. 20, 2006.
Office Action in U.S. Appl. No. 10/978,646, dated May 4, 2007.
Intl. Search Report and Written Opinion dated Mar. 13, 2007, Appl. No. PCT/US2006/042787.
Intl. Search Report and Written Opinion dated Mar. 21, 2007, Appl. No. PCT/US2006/046057.
U.S. Appl. No. 11/123,372, Office Action dated Feb. 27, 2007.
U.S. Appl. No. 11/124,313, Office Action dated Feb. 28, 2007.
U.S. Appl. No. 11/123,461, Office Action dated Mar. 7, 2007.
U.S. Appl. No. 11/123,809, Office Action dated Mar. 7, 2007.
U.S. Appl. No. 10/978,646, Office Action dated May 4, 2007.

* cited by examiner

FUEL DELIVERY METHOD FOR MELTING PLATE CANDLE

RELATED APPLICATION(S)

Not applicable.

FEDERALLY SPONSORED RESEARCH OR DEVELOPMENT

Not applicable.

BACKGROUND OF THE INVENTION

1. Field of the Invention

The present invention relates to a means for providing an improved fuel delivery method utilizing a wick clip or wick holder assembly in a melting plate candle or other candle assembly having a replaceable wick and/or fuel puck. This invention is most particularly designed to be used in a melting plate candle having means to provide a capillary feed between the wick holder and the melting plate, as well as in jar candles or conventional container candles.

2. Description of the Related Art

Clips which locate and secure wicks for candles and for devices which dispense vapors into the ambient air are well known in the art, and useful in many applications. In candles, such clips provide a means to position the wick for the most efficient provision of fuel, such as candle wax, to the flame, while in vapor dispensing devices, such wick clips secure a wick by which a vaporizable liquid is delivered from a reservoir to an exposed surface.

More recently, melting plate candles and simmer plate dispensers have been used to provide rapid melting of a solid fuel element and/or rapid dispensing of a vaporizable material to the atmosphere. An example of such a dispensing device is shown in U.S. Pat. No. 6,780,382, issued Aug. 24, 2004, in which a dispenser for active materials is shown. This reference, incorporated herein by reference, illustrates a melting plate dispenser of volatile materials comprising a solid fuel containing active material, a consumable wick, and a heat conductive base having conductive elements, and the configuration of such elements.

In application Ser. No. 09/747,525, filed Dec. 20, 2000, a melting plate candle comprising solid fuel, a consumable wick, a concave melting plate comprising a lobe by which heat is conducted from the flame upon the candle to the plate, and the configuration of such elements, are shown.

In addition to the above, application Ser. No. 10/780,028, filed Feb. 17, 2004, teaches a candle comprising solid fuel, a melting plate, a lobe that engages a wick holder which comprises a wick and which conducts heat to said lobe and to said melting plate. In this application, said wick holder engages said lobe in such a manner as to create a capillary flow of melted fuel to the wick itself.

In each of the above references, the melting plate candle provides a relatively rapid means for heating the solid fuel to its melting point, thereby improving efficiency of the candle. However, it has now been found that even more efficient, and more particularly, more rapid melting of the solid fuel may be achieved by means of specific modifications of the wick holding device. In addition, it has now been found that the combination of a consumable wick with a permanent wick provides a still further improvement, as set forth hereinafter.

SUMMARY OF THE INVENTION

The present invention, designed for use with a candle holder or dispenser of actives as described above, but suitable for use with most forms of container candles and/or dispensing devices, provides a means for a more rapid melting of the solid fuel element, resulting in a more rapid release of any volatile materials therein, and the creation of a more uniform pool of liquefied fuel for consumption, while also providing a means to combine both a consumable wick and a permanent wick in a single device. This goal is achieved by a combination of specific measures to extract heat from the flame on the consumable candle wick, and utilize this heat to maintain a permanent wick at a high enough temperature to maintain the ignition of fuel at this location. Moreover, the heat transfer means by which the permanent wick is heated also provides a capillary path for the delivery of fuel and at its furthest end, and constitutes the permanent wick itself. Such fins, comprising a capillary region between the two sides of the fin areas of the wick clip, may be referred to as capillary fins or capillary prongs.

Specifically, the preferred wick holder of the present invention comprises a wick holder designed to provide heat fins, a wick positioning holder, and a base preferably designed to not only engage a similarly shaped portion of the bottom of the container in such a manner as to prevent its easy displacement from the bottom of the container, but to also create a capillary flow of melted wax, or liquefied active containing material, between the wick holder itself and the portion of the bottom by which it is engaged. The heat fins of said wick holder, preferably provided as a pair of fins on opposed sides of the wick holder, are so designed as to be positioned in proximity to the main combustion zone of the flame upon the wick, which is held by said wick holder. That is, the tips of the heat fins are so located as to absorb considerable heat from the flame. Various means to accomplish this goal are available. One or both of the heat fins may be so shaped as to curve inwardly to a position whereby the tip absorbs heat from the flame, even as the flame flickers.

Preferably, the engaging and positioning means for the wick clip, preferably located on the bottom of the container near the center thereof, is a raised protrusion or pedestal, similar to a capillary lobe, and having a configuration by which the wick holder may be locked in place. Alternatively, the engagement means may comprise a depression in, or undercut portion of, the bottom of the container. The wick holder may comprise a ring of plastic or metal which engages said pedestal or depression, and has a portion which snaps over said pedestal in such a manner as to grip an undercut portion thereof. Alternatively, the wick holder may be designed so as to be inserted, with pressure, into a depression having a defined opening, and which then radially expands to resist removal from said opening, or engages a portion of said depression in such a manner as to inhibit removal there from without further radial compression of the wick holder. Exemplary of such designs are spider-type legs, or a skirt, which can engage, or snap around a central pedestal or bump having a depressed area between the top of the pedestal and the bottom of the container. Other means for lockingly engaging the wick holder to the capillary pedestal, or the bottom surface, of the candle container are available, and preferably constitute means which will prevent accidental displacement of the wick holder, but which may be released so as to permit replacement of the wick holder at the discretion of the consumer.

The present invention thus provides a candle, lamp device, or dispenser of an active material, capable of rapidly and completely melting a solid fuel to form a large liquid pool, thereby improving distribution of any volatile materials present in the fuel, and ensuring efficient and complete utilization of all of the fuel provided, while providing increased safety and convenient refilling. Further, the concept of the present invention offers highly decorative as well as functional candles, lamps, and dispensers, which may utilize a variety of gel and solid fuels, with the significant advantages of permitting rapid and convenient replacement of one fuel element by another at the desire of the consumer, without the need to clean or scrape the container in which said candle is utilized to remove a body of unburned fuel after the bulk of the previous fuel element has been consumed.

These and other embodiments of the invention shall be illustrated in the figures and description which follow.

DETAILED DESCRIPTION OF THE INVENTION

Ordinary candles comprise a vertical, self-supporting body or column of wax, with a substantially horizontal top and a central longitudinal wick which extends through and above the wax. The exposed portion of the wick above the solid wax is lighted by a flame, and the heat generated by the flame melts a small volume of the wax at the top of the candle, adjacent the wick, establishing a puddle or reservoir of molten wax to serve as fuel for the flame on the wick, and to release any volatile actives present therein. The capillary attraction of the molten wax and the wick, which is generally a structure of closely related fibers, causes the molten wax to travel through the wick to the flame, by which it is consumed. As the wax is consumed in this manner, the body of wax diminishes and the top surface thereof progressively lowers. The upper portion of the wick, extending above the lowering wax, is generally consumed by the flame. The flame in such a candle remains in the same position relative to the horizontal center of the candle, but decreases in height relative to the surface upon which the candle rests, from the start to the end of the burn, at which time all or at least most of the wax has been consumed.

Also well known are such candles as votive candles and tea lights. For purpose of discussion, tea lights shall be considered to be relatively small candles in which a body of paraffin is located in a container, having a wick centrally disposed, while votive candles shall be considered to be candles of similar size provided without a container. At the lower end of the wick is typically found a wick clip having a flat horizontal bottom surface, which functions to retain the wick in its perpendicular position, even as the paraffin is melted and liquefied by the heat of the flame. In most such votive candles and tea lights, the wick is a cotton material saturated with paraffin, and burns with the paraffin, thus being consumable. In such candles, or lights or warmers employing the same, the visible flame moves lower, or closer to the bottom surface of the container as the fuel and wick are consumed, down to the level of the bottom of the wick. Further, after consumption of all of the wax above this point in the unit, the container (of the tea light), the unburned wax, and the wick clip remain to be disposed of by the consumer. As a safety consideration in such candles, the wick is normally crimped or terminated at a point about 0.25 inches above the bottom of the wax, so as to cause the flame to extinguish above the bottom of the container, and to thus prevent the heat of the flame from reaching the surface upon which the candle is positioned, preventing damage to such surface, and reducing the likelihood of igniting possible contaminants such as burnt matchsticks remaining at the bottom of the candle, or carbonaceous remains of the consumable wick. Such an arrangement also has the detriment of leaving a small volume of unburned wax in the bottom of the container when the flame extinguishes.

As utilized herein, the term melting plate candle shall encompass the combination of a solid fuel element and a heat conductive container or holder for the fuel. The terms fuel container and fuel holder shall be meant to encompass a support plate or melting plate comprising means to contain and melt the fuel element, and a wick holder engaging a wick and said support plate, said wick holder comprising heat conductive elements, such as fins, referred to hereinafter as either wick fins or heat fins. Said wick holder shall also encompass a base having a skirt or legs configured to engage a complimentarily shaped pedestal portion of the support plate, and to transfer heat from a flame upon said wick to said melting plate. Thus, the support plate functions to hold the fuel element, to retain the wick holder, and to conduct heat to the solid fuel element to thereby melt said fuel element to provide a liquid fuel to feed to the flame via the wick. Moreover, the base portion of the wick holder engages, by the use of legs or skirt means, a pedestal on the surface of said support or melting plate in such a manner as to resist detachment from the melting plate, while also providing a means for transporting liquid fuel from the support plate to the wick by capillary action. Thus, the pedestal to which the wick holder is attached may be referred to as a capillary pedestal, whereas in conventional melting plate candles, in which no locking or attachment means is present to secure the wick holder to the base of the melting plate, the wick holder may be said to engage a capillary lobe. The capillary pedestal of the preferred embodiment of the present invention may thus be considered to be a capillary lobe having an undercut or other means by which a wick holder may be engaged so as to resist accidental displacement. The wick holder may thus be considered to be locked in place to the capillary pedestal, although it is removable by the consumer for replenishment of the wick and/or the fuel element, by exertion of sufficient force to overcome the engaging pressure. As will be appreciated, the manufacturer may provide melting plate devices, wicks and wick holder assemblies, and solid fuel elements, either together, or independently (separately), and the consumer may join the separate elements to form a melting plate candle, fuel burner, or dispenser of active materials, with the option to change wicks and fuel elements at will. In a preferred embodiment of the invention, the wick, wick holder, and fuel element may be provided as a unitary replacement element to be utilized with a separately provided melting plate.

An element of the present invention constitutes a capillary pedestal on the melting plate, which pedestal provides a locating device for a complementarily shaped wick holder, creates a site for capillary feed of fuel to the wick, and provides a means for heat transfer from the flame to both the melting plate and the solid fuel. The wick holder, in addition to providing a mounting means for the wick, has a base which closely conforms to the capillary pedestal in such a manner as to create a capillary feed by which melted wax flows to the wick as fuel. Moreover, the capillary pedestal of the present invention is configured so as to engage said wick holder in such a manner that it may not be easily or accidentally removed from said pedestal. This may be accomplished, as previously discussed, for example, by means of an undercut in the side of the pedestal, which undercut engages a complimentarily shaped leg or skirt of the wick holder, which leg or skirt may be made of a resilient material, such as a heat conductive metal, which is biased inwardly on the pedestal in the area of the undercut therein, so as to resist removal. This capillary pedestal and locking mechanism is set forth and claimed in U.S. patent application Ser. No. 10/934,434, filed Sep. 10, 2004, in the names of Kubicek et al.

In addition to the base and/or skirt of the wick holder being a heat conductive element, the wick holder preferably also provides an additional heat conductive element such as a fin or fins, which are in close proximity to the flame, and thereby conduct heat back to the wick holder base, and thus to the capillary pedestal, and thereby to both the melting plate and the fuel. It is to be understood that this arrangement of elements provides for much greater control of the degree of heating of the pool of melted wax, and the pool temperature, by virtue of the ability to control the amount of heat conducted to the pool by either the skirt of the wick holder or by the fins thereof. This may be accomplished by selection of the number of fins, for example, or control of the conductivity thereof, such as by choice of position relative to the flame, or material of construction. This in turn is most important in candles which dispense a volatile material, such as a fragrance, where a rapid temperature rise to the most effective temperature for volatilization of the active material is desired. Such a rapid temperature rise clearly results in a more rapid melt of the fuel element, and a more rapid dispensing of volatile material. In fact, with the present invention, it is possible to tailor a melting plate candle to a specific volatile active to be contained within a fuel element, by permitting control of the amount of heat conducted to the pool of melted fuel, and thus controlling the temperature thereof.

The material of which the melting plate and the heat fins are fashioned should be of high thermal diffusivity, i.e. have high thermal conductivity, low density, and low specific heat. The preferred materials may be such metals as aluminum and copper, but any easily shaped and high conductivity metal may be used. By use of such metals, one obtains the least resistance to heat transfer from the flame to the fuel puck. Moreover, the region of said fins between the flame and the wax or the base of the wick holder should be insulated, so as to prevent loss of heat to the surrounding atmosphere, by either radiation or convectional means. The insulating material may be any conventional non-combustible material which may be readily applied to the surface of the heat fins, by any conventional method. In addition, it is beneficial to extend one or more portions of the wick holder base outward into the wax puck, so as to preferably transfer heat directly to the fuel element, rather than to the melting plate base. This also has the benefit of minimizing the supply of liquefied fuel to the wick near the exhaustion of the fuel supply, thereby reducing the likelihood of flaring or re-ignition of the candle at the end of its life.

In accordance with the present invention, the wick clip and wick fin assembly is fashioned from a single piece of suitable metal, stamped from a sheet material, and folded over on itself to form a wick clip such as illustrated. The capillary fins, or capillary prongs of the wick clip, and the base of the wick clip, are formed by bending a flat section of metal together and then crimping, riveting, or welding them together. Due to the small capillary space between the metal sections of the fins or prongs, melted wax can wick up inside a fin or prong until it vaporizes and is burned by the flame on the consumable wick. The region between the sides of the fin or prong may adjusted by the addition of protrusion to establish a predefined capillary space, which could then help control the wicking rate to the flame. Similarly, channels or veins could be provided in the area between the sides of the fins or prongs. Such fins or prongs may thus be referred to as capillary fins. The inner surface of the fins could also be treated so as to reduce the spread of liquid wax, and thereby regulate flame size. Further, the area within the fin or prong could be sealed or welded to regulate the direction of fuel vapor, or the number of openings over which the fuel may exit from the fin or prong to combust. Preferably, the area near the end, in close proximity to the flame, serves as the exit point for the fuel vapor, as well as a point of maximum heat absorption from the flame upon the consumable wick. In this manner, less volatile fuels may be utilized in the melting plate candle, although such fuels are typically more difficult to ignite and more likely to extinguish.

Alternative aspects of the present invention provide for the fuel element to be provided as a separate element, puck, or votive, which is complementarily shaped relative to the wick holder, so as to fit around the wick holder in its position on the capillary pedestal of the melting plate. While it is possible for a permanent wick and wick holder assembly to be provided as a part of the melting plate, in the preferred embodiments of the invention the wick holder, wick, and fuel element are provided to the consumer as a single unit. Alternatively, the wick and wick holder may be provided as a single unit, with individual separate fuel units, perhaps containing differing fragrances, for example, to be combined with a melting plate. In this manner, wick holders of differing shape and configuration may be combined with fuel elements of appropriate configuration which differ in color or scent, for example.

In addition, it has been found beneficial to insulate the area of contact between the wick holder and the capillary lobe of the melting plate candle holder so as to cause the greatest amount of heat flow from the flame to the wick fins to the wax puck itself, so as to most rapidly melt the wax puck. Thus, it is to be noted that while the present invention is described in terms of a melting plate candle comprising a capillary lobe and complimentarily shaped wick clip base, it is possible to apply the invention to wick clips to be employed in candles comprising a non-conductive base, whereby the heat is transferred directly to the wax puck by means of the heat fins, rather than to both the wax puck and a heat conductive melting plate base. In either case, it is proposed that the highly heat conductive heat fins are so positioned as to capture the maximum heat output of the candle flame, that the heat fins be insulated in the area between the flame and the solid fuel element, with which the heat fins are in direct contact, and that maximum release of the heat from the wick fins to the solid fuel element be achieved. This may preferably be achieved by forming leaves or branches which extend from the fins, or from the wick holder base to which the heat fins attach, into the solid fuel element itself. Of course, the heat fins may also be so shaped as to maximize surface contact thereof with the solid fuel.

Accordingly, the melting plate is preferably comprised of a heat conductive material, such as a metal, although less conductive materials, such as glass or ceramic may be employed. The preferred material for use as the melting plate is polished aluminum, due to its high efficiency as a conductor of heat, its light weight, and for aesthetic reasons. It is also possible that the melting plate may constitute a non-conductive body having a conductive surface applied thereto, such as a less conductive surface having a thin layer of metal applied thereto. In this regard, it is noted that the surface of the melting plate may also have a coating of a surface tension modifying material applied thereto for purposes of preparing a self cleaning or easy cleaning melting plate. For example, a thin layer of a polytetrafluoroethylene material may be applied over a rough surface to provide a smooth wetting surface upon which molten wax will flow easily, and which will enable easy removal of solidified wax upon extinguishing the flame and allowing the candle to cool.

The melting plate, which may act both as a fuel container and a heat transfer means to heat the fuel, is shaped so as to collect the melted or liquefied fuel at its lowest point, at which point a wick is preferably located by means of a wick holder positioned upon a capillary pedestal, so as to ensure that all fuel is fed to the wick, whereby the maximum consumption of the fuel is achieved. Thus, the melting plate is preferably shaped as a bowl, or in the form of a funnel, with the lowest portion thereof preferably, but not necessarily, centered. The entire interior surface of the fuel container is preferably highly heat conductive, and supports, contains, and heats the fuel, although containers in which only a small portion of the interior surface acts as a melting plate are within the scope of the present invention. Candles employing such melting plates shall be referred to, collectively, as melting plate candles. The melting plate itself may, of course, be essentially flat, with raised edges or a surrounding wall to contain the melted fuel.

Moreover, the melting plate helps to control the shape and depth of the pool of fuel which is burned at the wick, and to maintain the constancy thereof. It is to be understood that the fuel utilized in the present invention may be initially in solid or gel form, but must be in liquid form for moving up the wick by capillary action to the flame, where it is consumed. Of course, the fuel also move up the interior of the fins or prongs of the wick clip as a liquid, up to the point at which it is vaporized and discharged in the direction of the flame on the consumable wick. Thus, the fuel used with the melting plate candle shall be such that it will not be transported by wicking action at ambient or room temperature, but requires heating to a liquefied state, i.e. melting, to be subject to capillary or wicking action. For convenience, the term solid fuel shall be used hereinafter to refer to fuel in either a gel or conventional solid state, such as conventional candle wax, preferably in the form of a hard, shaped body such as a votive, or "puck" of wax. It is also to be understood that the fuel consumed in the flame at the burning wick is drawn by the wick from a liquid pool of fuel, which pool is formed by melting the solid fuel, and heating said liquid pool by conductive heat transfer from the melting plate and heat exchange elements provided by the wick holder, in addition to the radiant heat from the flame on the wick. By the use of the melting plate and heat fin technology of the present invention in addition to the conventional radiant heating of the surface of the fuel, the size, volume, depth, and temperature of the liquid pool of fuel are better regulated. And, as a result of greater control of heat transfer to the fuel, a melted, liquid pool thereof is more rapidly formed and heated to a desired temperature. Because the speed of achieving a uniformly heated liquid pool of fuel is increased, a more efficient consumption of the fuel results, and a more complete usage of available fuel due to the decrease of fuel left unburned on the surface of the melting plate, as well as a more rapid and efficient release of any volatile active materials in said fuel, such as fragrances. In preferred embodiments of the present invention, a pool of liquid, i.e. melted, fuel rests upon the surface of the heat conductive melting plate. This pool of fuel may initially contain unmelted fuel in the solid state, as well as melted fuel, and the elevated temperature of the pool achieved by the present invention aids in assuring a complete melting of the solid wax puck and complete and optimized dispersal of any volatile active materials present in the fuel Generally, the melting plate device embodies both a melting plate and secondary heat conductive elements, which secondary elements are to be provided as part of the wick holder and are in close proximity to the flame, to ensure more uniform and rapid distribution of heat from the flame upon the wick. The wick is affixed in its preferred position by means of the wick holder. The primary wick, which is preferably a consumable wick, may be any filamentary body which is sufficiently sturdy, which will burn with a steady flame, and which is capable of drawing up the molten candle fuel by capillary action. Such a wick may be of any conventional consumable wick material, such as cotton, cellulose, nylon, or paper, but may be non-consumable as well. The wick holder and wick may preferably be located in the center of the candle, or may be off-center as desired. The presence of two or more consumable wicks, and associated wick holders with capillary fins and capillary pedestals, is also within the scope of the present invention. In the present invention, the primary wick is preferably positioned in a wick holder which engages the melting plate by means of an appropriately located capillary pedestal on the melting plate, which serves to locate the wick holder (and thus, the wick), to transmit heat from the flame on the wick to both the fuel and the melting plate, and by means of the capillary nature of the appropriately sized gap formed by the fit of the pedestal in relationship to the wick holder, as well as the capillary fins resulting from the relationship of the sides of the fins or prongs of the wick holder, to enhance flow of fuel to the wick. In the invention as set forth, the capillary fin or capillary prong acts as a permanent wick, providing a separate and distinct flame apart from the flame located at the consumable wick. Moreover, the wick holder is preferably configured so as to also engage the fuel element in a lock and key relationship and to position it on the melting plate in the preferred location.

A heat conductive element constitutes the melting plate itself, which may comprise portions formed, raised, or bent to be in closer proximity to the flame, such as a raised section of the plate, e.g. the upper edge of the raised side of the melting plate, or a lobe separate and distinct from the capillary pedestal. For example, the melting plate may constitute a bowl shaped container having its outer periphery in close proximity to the flame, such as a container in which the side wall of the bowl is formed so that the lip of the upper opening curves back toward the center of the bowl, and thus toward the flame. The melting plate may also have secondary heat conductive elements, such as one or more raised portions or lobes which act not only to absorb and distribute heat by conduction, but to channel or direct the flow of liquid fuel to the wick. Such raised portions may constitute areas of material having higher heat conductivity than surrounding areas of the container. In such examples, the support plate may comprise a less conductive material, such as glass, and the principal heat exchange may be by radiant heat and conducted heat by means of the primary heat conductive elements of the wick holder. It may thus be seen that the wick holder assembly, comprising a wick, and a fuel element, in conjunction with a base configured so as to complimentarily engage a capillary pedestal, may be utilized in any candle container comprising a capillary pedestal.

In the present invention, a capillary pedestal both engages and positions the aforementioned wick, wick holder, and fuel element in such a manner as to provide the most advantageous positioning thereof, as well as to create a capillary flow of melted fuel from the melting plate to the wick positioned in the wick holder, which is placed in such close relationship to the capillary pedestal as to create a very narrow gap between the pedestal and the wick holder. By virtue of this narrow gap, which may be from approximately 0.01 to about 0.04 inches, preferably about 0.02 inches, liquefied fuel rises to the wick for consumption. It should be noted that it is within the scope of the invention that the capillary action may be improved as a result of grooves cut in the pedestal, or in the wick holder, and that the wick holder may be held away from the pedestal by the presence of appropriately positioned and sized bumps located on either the pedestal, the wick holder, or the melting plate. Moreover, the capillary forming combination of elements may constitute a concave depression in the melting plate, rather than a raised male pedestal, and the wick holder in such case may be an appropriately shaped male member which fits closely within the depression so as to create a capillary gap between the members, by which fuel is fed to the wick, and having engagement means to prevent its accidental removal from said depression. Still further, it is contemplated that the capillary pedestal, in a male configuration, or a female depressed configuration, need not constitute a circular member, but may be of any shape, such as for example cylindrical, pyramid shaped, square, oval, triangular, or any other desired shape, in combination with a like-shaped and appropriately dimensioned wick holder and locking means. It is also to be noted that the capillary pedestal need not transmit liquid fuel to the wick at all parts of the perimeter of the capillary pedestal. For example, a circular capillary pedestal in conjunction with a circular wick holder need only create a capillary gap for a limited portion of its circumference, such as for 90, 180, or 270 degrees. Thus, the wick holder need not be in a close enough proximity to the pedestal throughout the total area of engagement therewith to provide a full capillary effect, but only in sufficient area to provide an adequate flow of fuel to the wick to maintain the flame upon said wick. A similar situation may exist with respect to the side elements of the fins or prongs of the wick clip, as long as sufficient capillary force is generated to provide fuel to the tip regions of said capillary fins or prongs.

Additionally, primary heat conductive elements are separate assemblies which are utilized in conjunction with the melting plate and consumable wick and wick holder. The primary heat conductive element may take the form of heat fins or heat conductive surfaces attached to the wick holder, and having either vertical or horizontal orientation or elements of both. In preferred embodiments, such heat conductive elements are heated by direct contact with the flame, and conduct such heat to both the melting plate and to the fuel so as to more efficiently heat the fuel. The heat conductive elements of the wick holder, exemplified herein as heating fins, although not limited to fins per se, and intended to encompass other heat conductive extensions of the wick holder which may serve this function, may be of any highly heat conductive material, and may be either formed as an extension of the wick holder or joined to said wick holder in such a manner as to conduct heat from the flame to that portion of the wick holder which is engaged by the capillary pedestal and/or the melting plate. The wick holder thus comprises fins, a means to hold the wick, the wick, and a base configured so as to engage the melting plate via a capillary pedestal or lobe, and to transfer heat from said fins to said melting plate. Suitable and exemplary, although clearly not the only possible heat fins are illustrated in U.S. Pat. No. 6,780,282, issued Aug. 24, 2004, incorporated herein by reference. Moreover, the fins should be insulated in that region below the flame in which they are exposed to the ambient atmosphere, so as to prevent radiation and loss of heat to the surrounding area.

It is to be understood that the wick holder and associated primary heat conductive elements are meant to be so situated and shaped as to engage or interlock with a replaceable solid fuel element. In a similar fashion, the melting plate and/or the fuel container may be formed in such a manner as to permit placement of fuel elements of specific configuration, such as wax pucks having a complementary configuration, for example, in a preferred position in proximity to the heat conductive elements themselves, and/or to the wick holder, in such a manner as to maximize heat transfer from the melting plate to said fuel elements. In the most preferred embodiment, additional heat conductive elements are present as an element of the wick holder, in the form of extending legs or leaves from the base of said wick holder into the body of the solid fuel element. In said most preferred embodiment of the invention, there is a capillary pedestal present on the melting plate, positioned in such a manner as to also transfer heat to the fuel element, and configured so as to engage a wick holder holding a consumable wick and having one or more heat conductive capillary fins, and a fuel element such as a wax puck. Further, the engagement of the wick holder with the capillary pedestal is such as to provide a capillary effect between the two for feeding fuel to the wick. In this embodiment, the consumer may purchase a replacement fuel element comprising a wax puck and a wick holder and wick, configured so as to engage a matching capillary pedestal on the melting plate in such a manner as to position the fuel element and the wick holder, and having a heat conductive element in the appropriate location to most efficiently melt the fuel element. Alternatively, the consumer may purchase an assembly comprising a wick holder and wick, with separately available appropriately shaped fuel elements.

The use of the melting plate technology of the present invention may also provide such advantages as elimination of tunneling, significant reduction of retention of wax at the conclusion of the burn, and elimination of walking or off-center wicks, while also giving a larger pool of liquid wax with a relatively small flame in a relatively short time period. In addition, the container may be of almost any shape desired, providing for great aesthetic possibilities, which are further enhanced by the presence of permanent wicking means in the form of the capillary fins. Since the fuel element, either alone or in combination with a wick and wick holder, may be provided as a separate unit, the consumer may be provided a great number of choices as to the color, content, and nature of the fuel, and the configuration of the fuel element may be varied to provide a large choice of shapes, such as seasonably decorative items. For example, shapes such as pumpkins may be provided for Halloween, wreaths for Christmas, and flowers for all seasons. In addition, the fuel element preferably is configured as to cooperatively engage both the melting plate and the wick holder, which wick holder in turn engages the capillary pedestal on the melting plate, in such a manner as to provide the consumer the greatest degree of ease in placement of the fuel element in optimal position in the melting plate candle, with the least possibility of incorrect placement. Further, the melting plate or support plate may have decorative features, such as designs, embossed, etched, printed, or stamped thereon.

Accordingly, the present invention provides a melting plate candle, wherein said candle comprises a container for a fuel element comprising a fuel selected from the group consisting of paraffin, beeswax, montan wax, carnauba wax, microcrystalline wax, polyvinyl acetate, fatty alcohols, fatty acids, fatty esters, and gels incorporating such fuels, in a form selected from the group consisting of pucks, donuts, chips, slivers, balls, pellets, shavings, particulates, cubes, discs, three dimensional shapes, and wafers, or in any other suitable shape. Said fuel element may optionally further comprise such volatile active materials as fragrances, air fresheners, deodorizers, odor eliminators, odor counteractants, insecticides, insect repellants, herbals, medicinal substances, disinfectants, sanitizers, mood enhancers, aroma therapy compositions, and the like. Such solid fuel may be colored for decorative effect, if so desired, and may be shaped to fit any given configuration of melting plate and/or wick holder. For example, the bottom of a solid fuel element should be curved complementarily to the shape of the melting plate upon which it is to rest, and have melting temperatures above ambient, but below the flame temperature of a wick burning such fuel.

These and still other advantages of the present invention will be apparent from the description of the figures which follows, which description is merely of preferred embodiments, and not indicative of the full scope of the invention.

Figure 1:
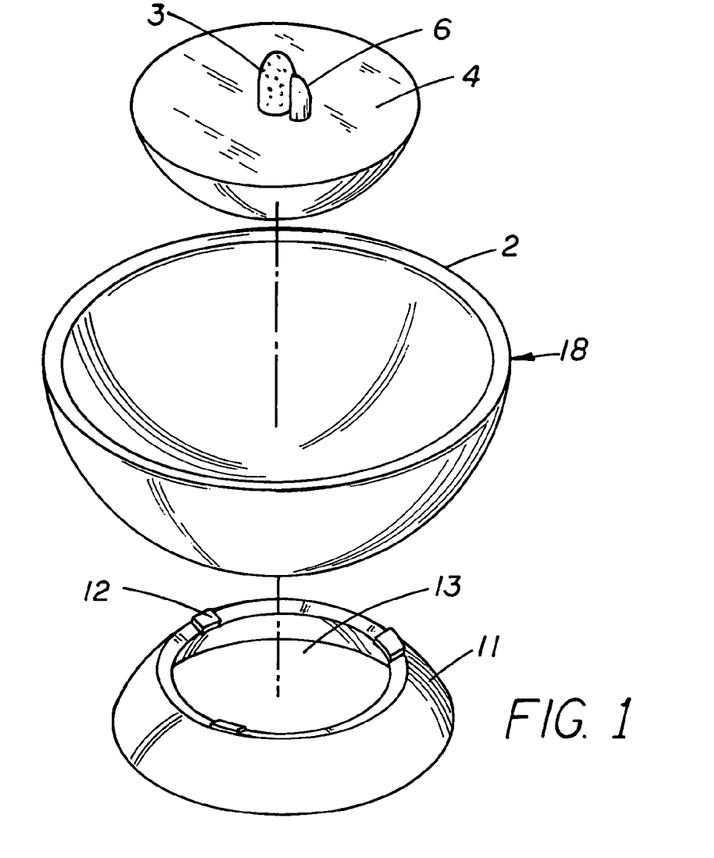
FIG. 1 illustrates the basic concept of a melting plate candle of the prior art, in simplified perspective view, of which the present invention constitutes an improvement.
Figure 2:
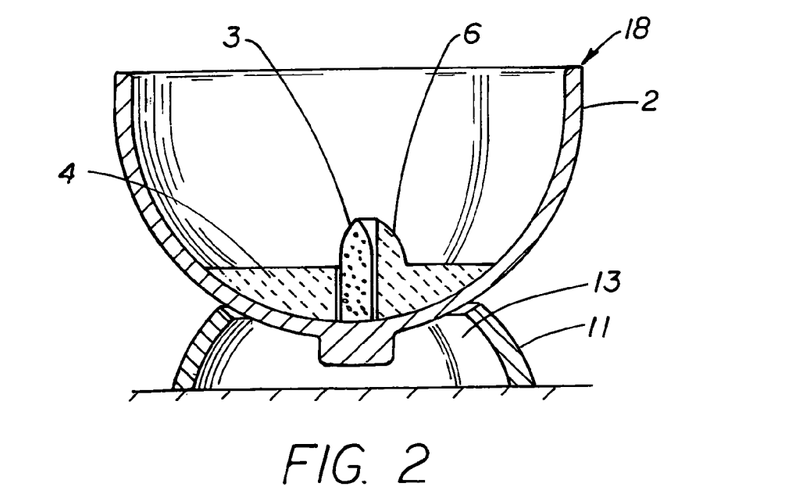
FIG. 2 illustrates a basic melting plate candle, in simplified cross section, absent the locking wick holder and other improvements of the present invention.

FIGS. 1 and 2 illustrate the broad concept of a melting plate candle in its most basic form, such as set forth in Ser. No. 09/747,525, filed Dec. 20, 2000, incorporated herein in its entirety by reference. The teachings of said pending patent application do not illustrate the capillary pedestal and wick holder assembly of the present invention, nor the primary heat conductive members comprising heat fins passing through the hottest region of the flame with regions thereof insulated to prevent heat loss to the atmosphere. As illustrated, a heat conductive melting plate container, 2, is provided, which transfers heat obtained from the heat source, a flame (not shown) located on wick 3, by means of heat conduction, to the solid fuel element, 4, which rests upon the surface of the melting plate. For purposes of illustration, and for clarity, but intending no limitation, the wick is illustrated in FIGS. 1 and 2 as being of a relatively large diameter, rather than as a fibrous wick of small diameter. It is to be understood that the wick is positioned within and attached to the solid fuel element, 4, such as with a wick clip (not shown in FIGS. 1 and 2). The melting plate, 2, as shown in FIGS. 1 and 2, is heated directly by a flame on the wick, 3, by radiation, as a result of the melting plate being shaped so as to have a portion, shoulder 18, in proximity to the flame, the diameter of the melting plate bowl being such as to permit the inner surfaces thereof to absorb appreciable amounts of heat from the flame.

The melting plate of FIGS. 1 and 2 is shaped so as to have a raised outer shoulder, 18, thereby containing the resultant pool of melted fuel. It is to be understood that the melting plate may be in the form of a tray, bowl, concave plate, or other configuration which is capable of holding a pool of hot liquid fuel, and is preferably shaped so as to funnel or channel the liquefied, i.e. melted, fuel to the wick. The melting plate may constitute a container in itself, as shown, or may be surrounded by a separate container. In the embodiment shown in FIGS. 1 and 2, the melting plate rests upon a non-conductive base, 11, or legs of non-conductive or insulating material, so as to permit placement upon a table, counter, or other surface. The non-conductive base, as illustrated, comprises contact points, 12, so as to minimize the amount of contact between the base and the melting plate, and to create an insulating air gap, 13, between the melting plate and the surface upon which the assembly rests.

The melting plate may be of any heat conductive material, such as brass, aluminum, steel, copper, stainless steel, silver, tin, bronze, zinc, iron, clad materials, heat conductive polymers, ceramics, glass, or any other suitable heat conductive material or combination of such materials. As shown in FIG. 2, the fuel is preferably located in direct contact with the surface of the melting plate, 2, which plate may, if desired, be constructed so as to have a non-conductive lower surface, so that the melting plate may rest upon a table surface or such. Such a configuration may result from a clad material, a conductive melting plate material coated on the external surface with a non-conductive material, a non-conductive material having an insert of a heat conductive material, or other suitable arrangements to permit the melting plate to be cool enough on the bottom surface to permit ease of handling, and/or placement upon surfaces not suitable for contact with heated bodies.

The wick, 3, preferably constitutes a conventional consumable wicking material, such as such as cotton, cellulose, nylon, or paper, or the like, which by capillary action will carry liquid fuel to the flame. Alternatively, non-consumable wicks may comprise such materials as porous ceramics; porous metals; fiber glass; metal fiber; compressed sand, glass, metal, or ceramic microspheres; foamed or porous glass, either natural or man-made, such as pumice or perlite; gypsum; and chalk. However, for purposes of the present invention, the use of conventional consumable wicks is preferred. The wick, 3, may be located in the center of the melting plate, 2, or may be off-center as desired, provided that the melting plate is configured so as to channel or funnel melted fuel to said wick. As illustrated, the wick may be positioned in conjunction with a starter bump, 6, of wax in the top surface of said fuel element, 4, for ease of lighting. The presence of two or more wicks is also within the scope of the present invention. The wick is provided in conjunction with the wick holder assembly, the preferred configuration of the wick holder being such as to cooperatively engage a complimentarily shaped capillary pedestal, 22, on the melting plate, as discussed hereinafter.

Figure 3:
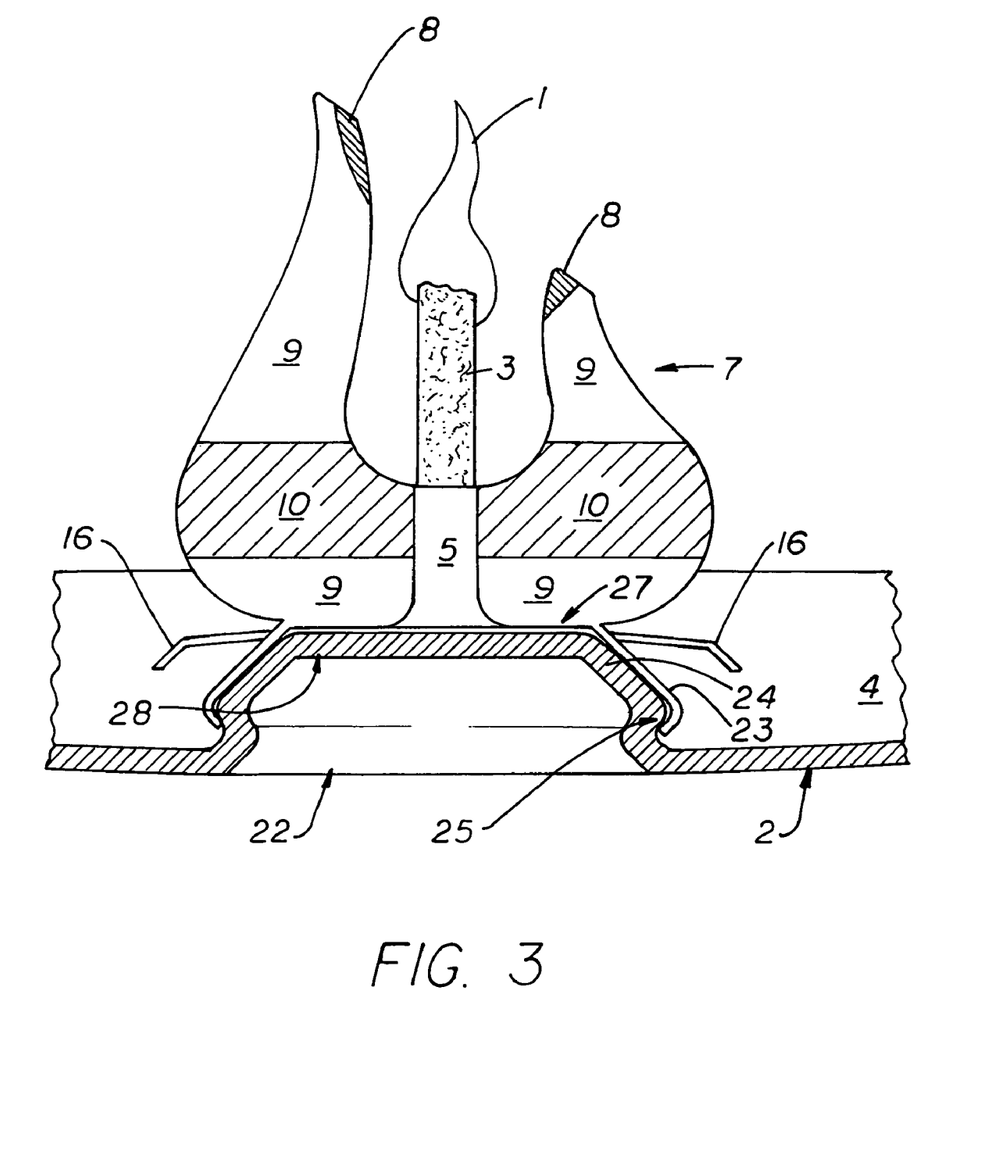
FIG. 3 is a simplified cross section of a melting plate candle, showing the capillary pedestal, a suitable locking wick holder with fins for use in the present invention, and the relationship between the elements.

FIG. 3 illustrates a melting plate container, 2, comprising a concave base, and having a raised pedestal or protrusion, 22, located near the center thereof, said pedestal being shaped so as to engage the legs or skirt, 23, of a wick holder, 7. The wick holder itself is comprised of a central wick holding means, 5, a wick, 3, and capillary heat fins, 9, located so as to absorb heat from a flame, 1, upon said wick mounted in said wick holder, and to permit flow of said heat from said flame to said base of said melting plate container, 2, and to the solid fuel element, 4. Areas 8, of the tips of said capillary fins, 9, are indicated as being potential permanent wicks in accordance with the present invention. Further, the fins are provided with insulated areas, 10, between a point below the closest point of exposure of the fin to the flame to a point near or below the surface of the solid fuel element. The legs or skirt, 23, of said wick holder fit in close proximity to the sides, 24 of said pedestal, 22, and engage an undercut, 25, in the side surface of said pedestal, by means of shoulder 26, in such a manner as to resist removal there from. The legs or skirt, 23, and the base, 27, of said wick holder and the sides, 24, and top, 28, of said pedestal are in close proximity, so as to permit maximum resistance to separation, and so as to create a gap resulting in a capillary flow of melted wax from the bottom of the melting plate container, 2, to the top of said pedestal, 28. In addition, highly heat conductive leaves or branches, 16, extend outward from the bottom of said wick holder into the body of the fuel element, so as to assist in rapid melting thereof. Such leaves or branches are preferably of the same material as the base of said wick holder. The bottom, 27, of said wick holder is shown to be in close proximity to the top, 28, of said pedestal, assuring a rapid and even flow of liquefied fuel to the wick, held in position so as to contact said fuel by wick holding means 5. Although the invention is illustrated in terms of a melting plate candle, it may be equally as effective in the context of a candle jar, tea light, or votive holder.

Figure 4:
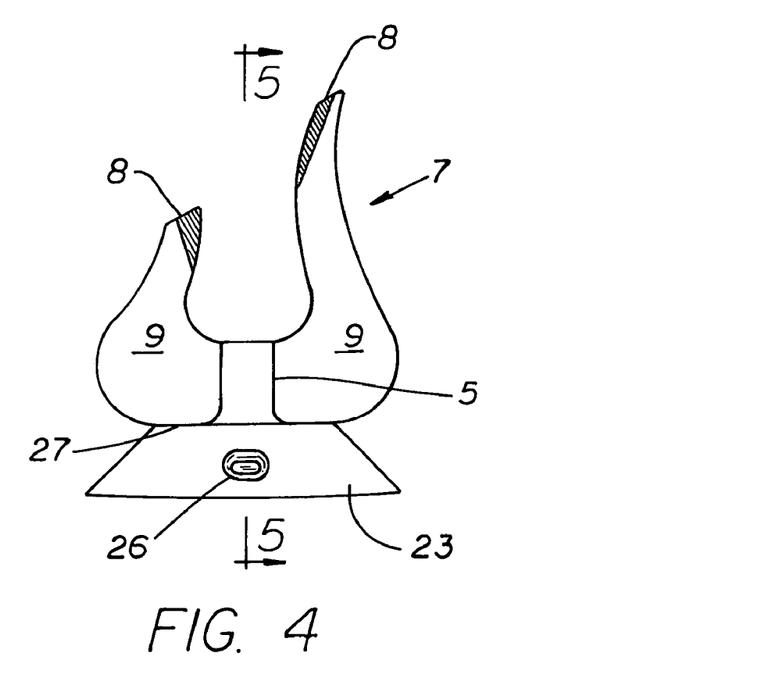
FIG. 4 is a profile view of a wick clip of the present invention, specifically illustrating areas of the heat fin which may potentially act as a permanent wick.

In FIG. 4, the capillary wick clip, 7, of the present invention is shown, with capillary fins 9 rising from the base of the wick holder, 27. At the inner surface, relative to the position of a flame on a wick held in position by wick retention means 5, of the capillary fins, areas 8 are indicative of areas capable of acting as permanent wicks. The skirt, 23, of the wick holder, 7, has a shoulder means 26, by which said wick holder is held to a pedestal (not shown) on the surface of a melting plate.

Figure 5:
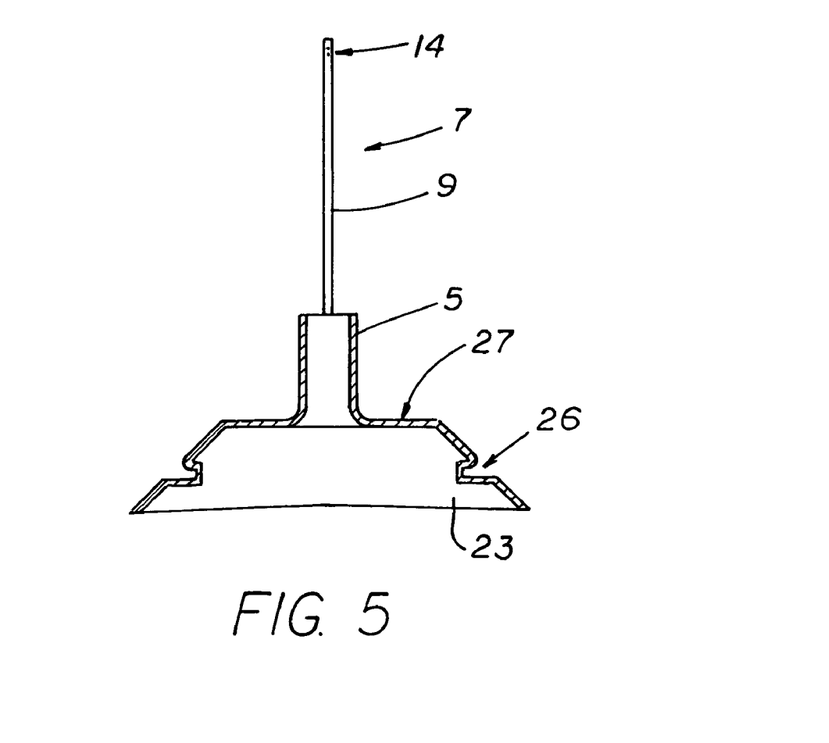
FIG. 5 is a sectional view of the wick clip of FIG. 4, taken on line A-A, showing the relationship of the heat fins to the wick clip base.

FIG. 5, a side view taken on line 5-5 of FIG. 4, illustrates the wick clip, 7, in profile. Capillary fin 9, having a capillary gap between the surfaces of said fin, may receive liquefied wax from a consumable wick (not shown) held in wick retention means, 5, atop the base of the wick holder. The skirt, 23, of said wick holder had a shoulder, 26, by which said skirt is positioned on a pedestal on a melting plate, or in a suitable candle container. Liquefied wax received from said consumable wick then travels, by capillary action, up the capillary fin, 9, to a point at which it is vaporized, and the vapor is discharged through exit openings 14 and ignited by the flame on the consumable wick. The area of capillary fin 9 where this release of vaporized fuel through openings 14 occurs is thus a potential non-consumable wick area, 8.

Figure 6:
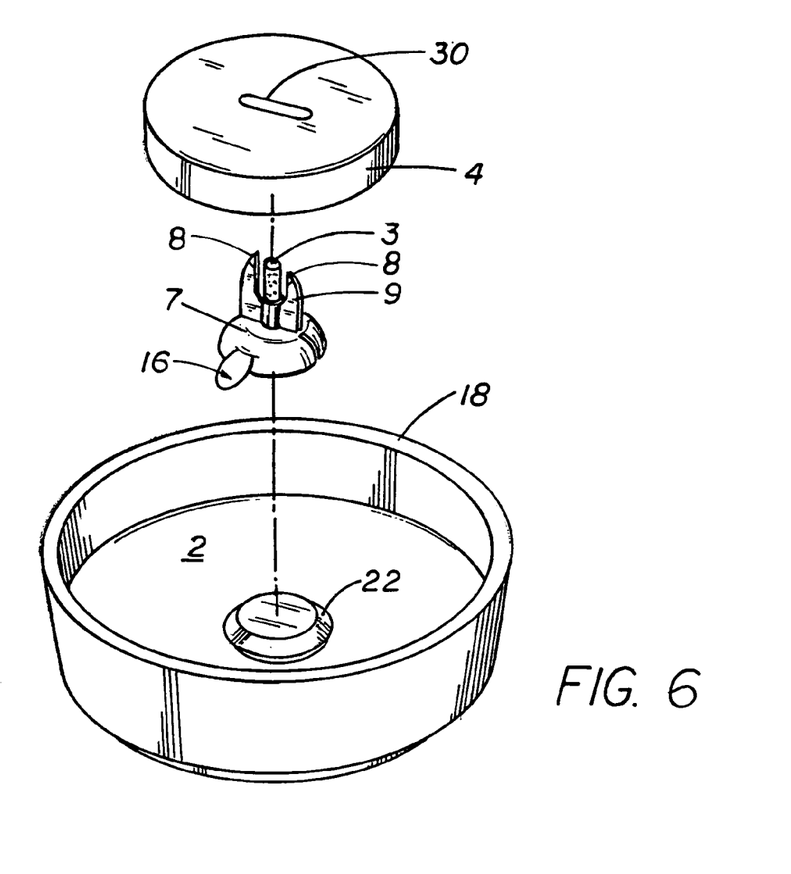
FIG. 6 is an exploded view of a melting plate having a capillary pedestal, with a wick holder as described herein with fins and incorporated wick, and a fuel element.

In FIG. 6, an exploded perspective view of the invention is shown, with a bowl shaped melting plate container, 2, which comprises a capillary pedestal, 22, located in approximately the center thereof. A wick holder, 7, is shown above the capillary pedestal, the wick holder being shaped in such a manner as to fit closely over said capillary pedestal, and to tightly engage an undercut therein so as to be locked in position. The wick holder, as illustrated, further comprises the wick, 3, and capillary heat fins, 9, with areas suitable for use as a potential non-consumable wick, 8, and a heat conductive leaf or wing 16. A solid fuel element, 4, is shown, having a cut out portion, 30, through which the heat fin and wick assembly may pass, so as to place the wick in close proximity to the top surface of said fuel element. The solid fuel element is shown as a wax puck, although other shapes may clearly be used within the scope of the present invention. To prevent difficulty in lighting the wick, a starter bump of fuel may be provided in close proximity to the wick, 3. As illustrated in FIGS. 1, and 2, this bump is most easily molded directly into the shape of the fuel element, and provides a ready source of liquid fuel to the wick when a match or other appropriate source of flame is employed to start the wick burning, which source of flame will melt the starting bump to thus create an initial pool of liquid fuel.

Figure 7:
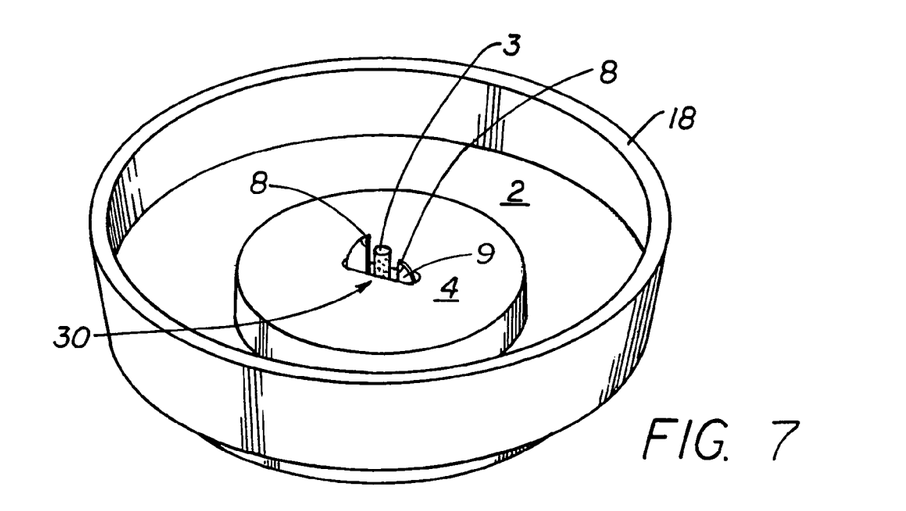
FIG. 7 is a perspective view of the assembled melting plate, wick holder, and fuel element of FIG. 6.

FIG. 7 shows the embodiment of FIG. 4 in operational configuration, showing the relationship of the elements in position for lighting of the wick, 3, wherein the melting plate, 2, is shown with a fuel element, 4, positioned on the capillary pedestal (22, not visible) and centered around a wick holder assembly with the capillary heat transfer fin, 9, and wick, 3, extending through the opening, 30.

Thus, when using a solid fuel, such as wax, in conjunction with a heat conductive wick holder, solid fuel refill units may be shaped to fit the shape of the melting plate, with a specific relationship to the wick holder, which itself is engaged with the melting plate by a locking means. For example, the melting plate may be a decoratively shaped container, and wax may be provided in the form of refills specific for the container shape selected, such as round, square, oval, rectangular, triangular, or otherwise, so shaped that the wick holder assembly incorporated with the wax refill unit will fit and engage a complementarily shaped capillary pedestal.

The use of a melting plate with additional heat conductive elements, such as the partially insulated capillary heat fins, offers a number of distinct advantages. First, it permits a larger pool of liquid fuel, due to improved heat conduction into the fuel, which results in more rapid formation of the pool. This in turn allows better regulation of the size and shape, as well as the temperature, volume, and depth of the liquefied wax pool to allow more efficient use of fuels present. In fact, melting plates of the present invention permit ease of refill, with little or no cleaning. In most instances, no cleaning is required, but if desired, the plate may be conveniently washed in a manner such as a dish, plate of bowl is washed, in a wash basin or in a dishwasher. In addition, the use of capillary heat fins creates the possibility of having both a consumable wick and a non-consumable wick in use, in the same candle, at the same time. The use of a capillary pedestal in the heat plate, in conjunction with capillary heat fins on the wick holder, also reduces or eliminates retention of solidified excess fuel when the candle burns out, and permits more complete and uniform burning of fuel elements which are other than round, i.e. square, oval, triangular, or in the shape of a flower or decorative object, etc. Further, the melting plate technology in conjunction with a capillary pedestal and complimentary wick holder with capillary fins, results in devices which may be self extinguishing, and improvements in or elimination of typical burning problems encountered with candles, such as tunneling, drowning, collapsing, cratering, and wick drift. Candles utilizing the melting plate technology of the present invention are also more forgiving of formulation or process variances. And, more importantly, the presence of a locking configuration of the wick holder and the capillary pedestal provides a margin of safety and convenience not previously available.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

INDUSTRIAL APPLICABILITY

The melting plate and heat conductive element candles of the present invention, utilizing a capillary pedestal and correspondingly shaped locking wick holder having capillary fins which are adjacent to the hottest portion of the flame upon the wick, but are elsewhere insulated to prevent heat loss, can be used in connection with a large variety of solid fuels. The conductive materials of which the melting plate and heat fins may be constructed are commonly available, and the various configurations are readily produced. There is considerable interest for candles having extended burn times, and for refillable candles or solid fuel lamps, particularly for melting plate candles which are resistant to accidental release of the wick holder assembly.

We claim:

1. A candle comprising a meltable solid fuel element, a melting plate upon which said fuel element rests, a wick holder comprising a wick retainer and a capillary heat conductive fin above the wick retainer positioned immediately adjacent to a flame position upon a wick retained by the wick retainer so as to collect heat from a flame upon said wick and to conduct such heat to said fuel element and to said melting plate, wherein said heat conductive fin fully defines a path capable of causing capillary movement of liquefied fuel supply from the wick to the flame.

2. The candle of claim 1, wherein said fuel element further comprises one or more volatile active materials.

3. The candle of claim 2, wherein said wick holder comprises at least two heat conductive capillary heat fins which are heated by said flame, conduct heat to the fuel element whereby additional fuel is liquefied, and wherein the capillary heat fins return such liquefied fuel to the flame by capillary action therethrough for consumption thereof, thereby creating a non-consumable wick.

4. The candle of claim 3, wherein said meltable solid fuel element comprises a replaceable fuel element cooperatively engaging said heat conductive melting plate and wick holder.

5. The candle of claim 1, wherein the path is defined between two adjacent surfaces of the same fin.

6. A candle as set forth in claim 3, wherein said melting plate further comprises a raised heat conductive portion by which heat is conducted from a flame upon said wick to said melting plate and to said solid fuel element whereby a pool of heated liquid fuel is created, said melting plate being configured to cause the flow of said heated liquid fuel toward said wick holder.

7. The melting plate candle of claim 1, wherein said wick holder is configured so as to engage a capillary pedestal on said melting plate.

8. The melting plate candle of claim 1, wherein said wick holder further comprises heat conductive members configured so as to transfer heat from said heat conductive fins to said solid fuel element.

9. A candle comprising a meltable solid fuel, a support plate upon which said fuel rests, and a pedestal located on said support plate which cooperatively engages the base portion of a wick holder comprising a wick, said wick holder conducting heat from a flame upon said wick to said solid fuel and said support plate by means of heat fins which contact said flame, said fins being insulated so as to inhibit heat loss from said fins to the atmosphere between said flame and said solid fuel, and each of said fins having an internal space therein extending between the wick and a distal tip of the heat fin so as to create capillary flow of melted fuel to the distal tips of the heat fins in proximity to said flame.

10. The candle of claim 9, wherein said wick holder comprises a plurality of heat conductive fins.

11. The candle of claim 10, wherein said meltable solid fuel comprises a replaceable fuel element cooperatively engaging said support plate, pedestal, wick holder, and heat conductive fins.

12. The candle of claim 10, wherein said support plate further comprises a heat conductive portion by which heat is conducted from a flame upon said wick to said solid fuel element, whereby a pool of heated liquid fuel is created, said support plate being configured to cause the flow of said heated liquid fuel toward said wick holder.

13. The candle of claim 9, wherein said support plate is treated so as to be self cleaning.

14. A candle comprising a fuel holder comprising a heat conductive surface shaped to hold and melt a solid fuel material included in a replaceable solid fuel element further comprising a wick holder including a consumable wick extending upwardly from a wick retainer and capillary heat fins above the wick retainer, and to form a pool of liquid fuel, said surface further comprising a capillary pedestal which lockingly engages said wick holder, wherein said capillary heat fins are in close proximity to a flame on said wick and conduct heat from said flame to said fuel element, each of said capillary fins fully defining a capillary path extending upwardly from the wick to a position immediately adjacent the flame, wherein each capillary path is capable of providing capillary flow of liquefied fuel up the respective fin to a point where said liquefied fuel is vaporized, said vaporized fuel then exiting said fins through exit openings in proximity to said flame, whereby said fuel is consumed.

15. The candle of claim 14, wherein said replaceable fuel element is configured to cooperatively engage said wick holder.

16. The candle of claim 14, wherein said replaceable fuel element further comprises one or more volatile active materials.

17. The candle of claim 14, wherein the replaceable fuel element further comprises a starter bump on the top surface thereof, in close proximity but not in contact with said consumable wick for ease of lighting said wick.

18. The candle of claim 15, wherein said heat conductive surface further comprises raised heat conductive lobes.

19. The candle of claim 14, wherein said heat conductive surface is treated so as to be self cleaning.

20. A replaceable fuel element for a melting plate candle, said fuel element comprising a solid fuel material cooperatively and a wick holder, wherein said fuel material engages said wick holder, said wick holder comprising a base portion configured so as to lockingly engage a capillary pedestal on said melting plate candle, and further comprising a wick retainer extending upwardly from the base portion and capillary heat fins above the wick retainer, wherein a wick is retained in an upright position by the wick retainer, wherein each capillary heat fin defines a capillary path extending between the wick and a flame position on the wick, and wherein the capillary heat fins conduct heat from said flame to said fuel element into said fuel element.

21. The fuel clement of claim 20, further comprising a volatile material.

* * * * *

UNITED STATES PATENT AND TRADEMARK OFFICE
CERTIFICATE OF CORRECTION

PATENT NO. : 7,413,435 B2
APPLICATION NO. : 10/938453
DATED : August 19, 2008
INVENTOR(S) : Elizabeth J. Jameson et al.

It is certified that error appears in the above-identified patent and that said Letters Patent is hereby corrected as shown below:

On the Title Page, Item (75)

Inventors: Add --Cory J. Nelson, Racine, WI (US); Matthew S. Montei, Racine, WI (US); Paul E. Furner, Racine, WI (US)--

Column 16, Line 42-43: replace "a solid fuel material cooperatively and a wick holder, wherein said fuel material" with --a solid fuel material and a wick holder, wherein said fuel material cooperatively--

Signed and Sealed this

Eighth Day of September, 2009

David J. Kappos
*Director of the United States Patent and Trademark Office*